United States Patent [19]

Yoshikumi et al.

[11] 4,315,851

[45] Feb. 16, 1982

[54] PHARMACEUTICAL COMPOSITION HAVING ANTITUMOR ACTIVITY

[75] Inventors: Chikao Yoshikumi, Kunitachi; Takayoshi Fujii, Tokyo; Masahiko Fujii, Tokyo; Kenichi Matsunaga, Tokyo; Yoshiharu Oguchi, Yono; Koichi Niimura, Sayama, all of Japan

[73] Assignee: Kureha Kagaku Kogyo Kabushiki Kaisha, Tokyo, Japan

[21] Appl. No.: 103,474

[22] Filed: Dec. 14, 1979

[30] Foreign Application Priority Data

| Dec. 29, 1978 | [JP] | Japan | 53/161388 |
| Nov. 2, 1979 | [JP] | Japan | 54/142152 |
| Nov. 2, 1979 | [JP] | Japan | 54/142153 |

[51] Int. Cl.$^3$ .............................................. A61K 39/44
[52] U.S. Cl. .......................... 260/112 B; 260/112 R; 424/85
[58] Field of Search ..................... 260/112 R, 112 B; 424/85

[56] References Cited

U.S. PATENT DOCUMENTS

| 3,947,352 | 3/1976 | Cuatrecasas et al. | 260/112 R X |
| 3,983,001 | 9/1976 | Coupek et al. | 260/112 R X |
| 4,017,471 | 4/1977 | Davies | 260/112 B |
| 4,046,722 | 9/1977 | Rowland | 260/112 B X |
| 4,093,607 | 6/1978 | Sela et al. | 260/112 R X |
| 4,123,427 | 10/1978 | Daniel | 260/112 R X |
| 4,160,018 | 7/1979 | Bjorkjund | 424/12 |
| 4,195,017 | 3/1980 | Bogoch | 260/112 R |
| 4,223,005 | 9/1980 | Teodoresev et al. | 435/7 X |
| 4,228,237 | 10/1980 | Hevey et al. | 435/7 |

OTHER PUBLICATIONS

J. Immunol. 113, pp. 948–953, Davphinee et al., 1974.
Cancer Research, 35, 1182–1186 (1975), Levy et al.
Clin. Chem. 22/6, 726–732 (1976), Broughton et al.
Science, vol. 169, 1970, pp. 68–70, Moolten et al.

*Primary Examiner*—Howard E. Schain
*Attorney, Agent, or Firm*—Wegner & Bretschneider

[57] ABSTRACT

Disclosed is a novel pharmaceutical composition having antitumor activity without causing pyrexia and anaphylaxis formed by an amido bonding between an antibody obtained by the purification of the antibody to tumor antigen via affinity-chromatography and an antitumor substance.

8 Claims, 8 Drawing Figures

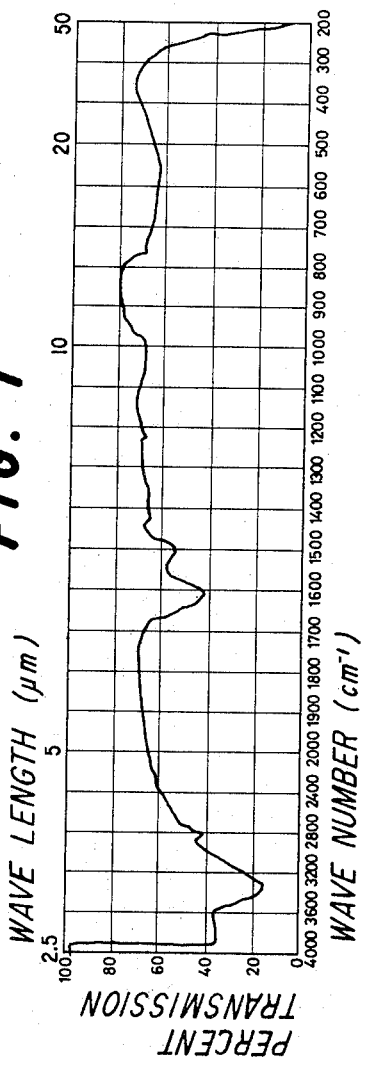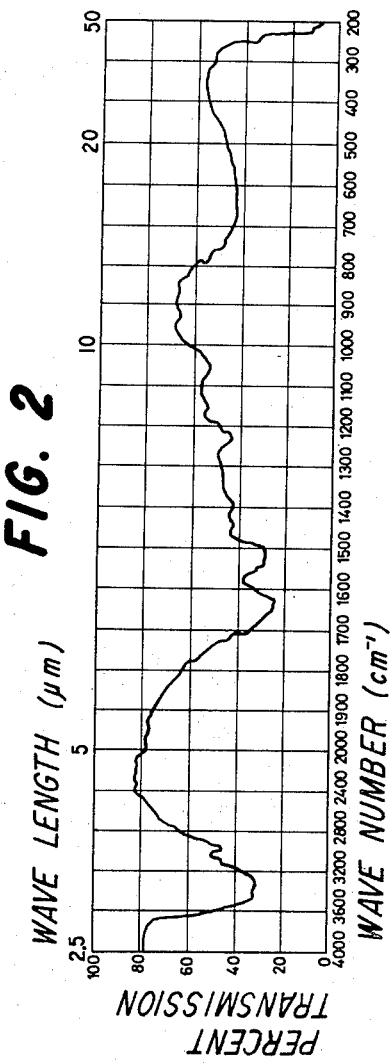

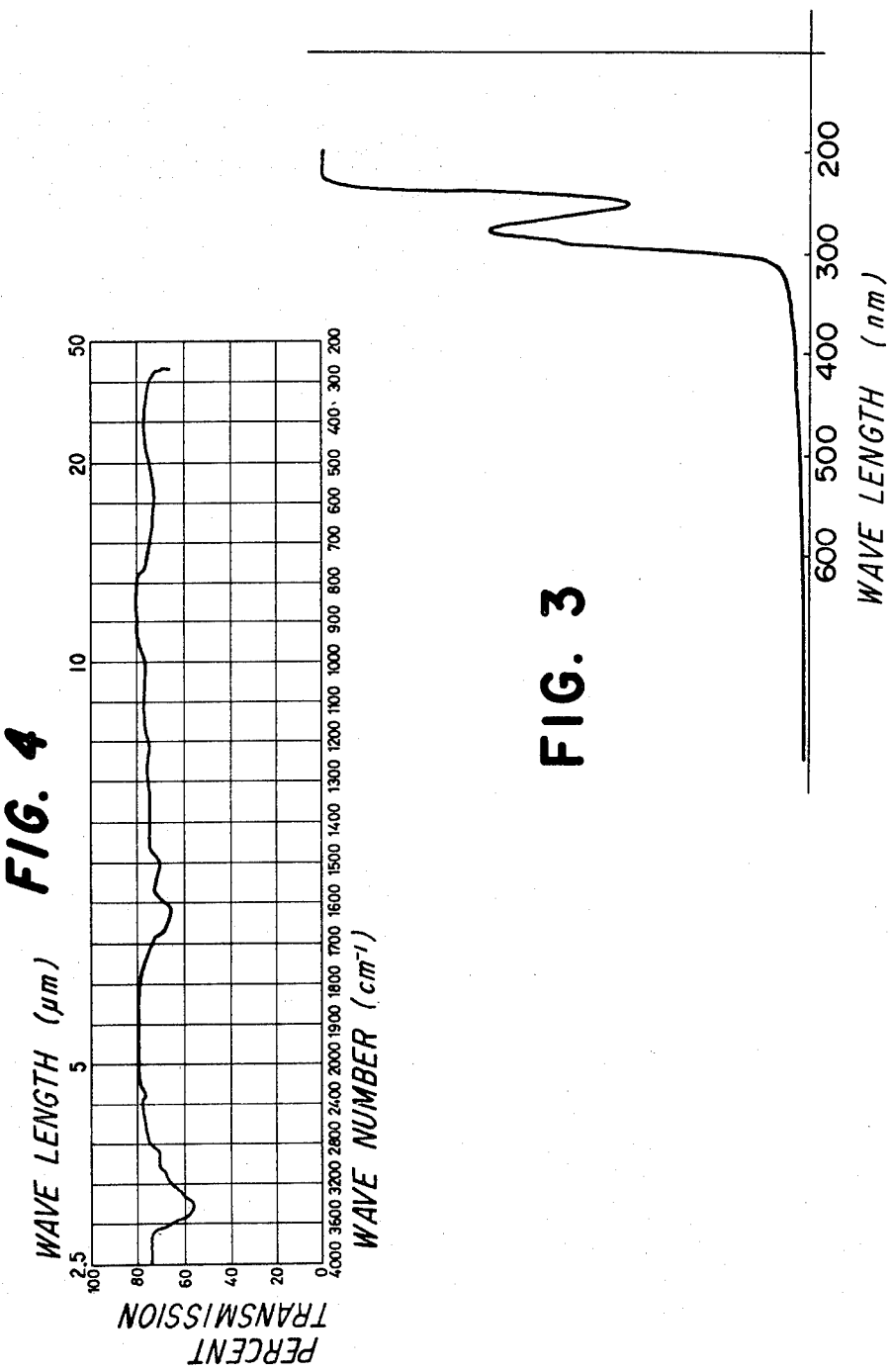

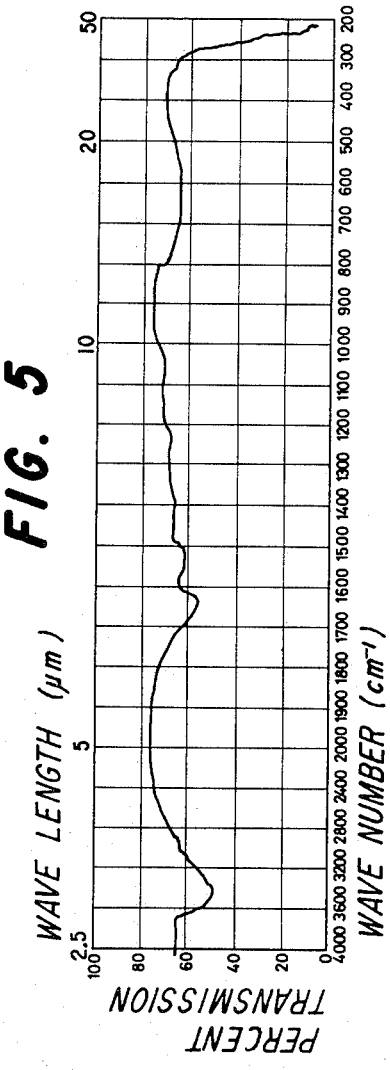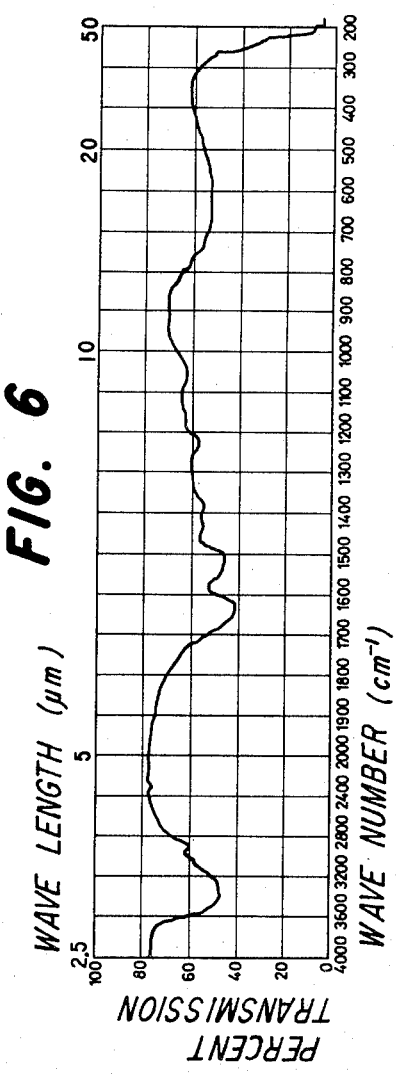

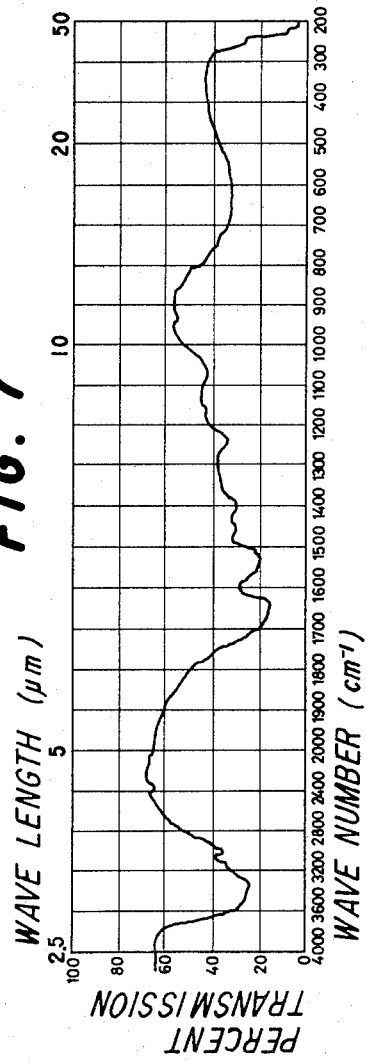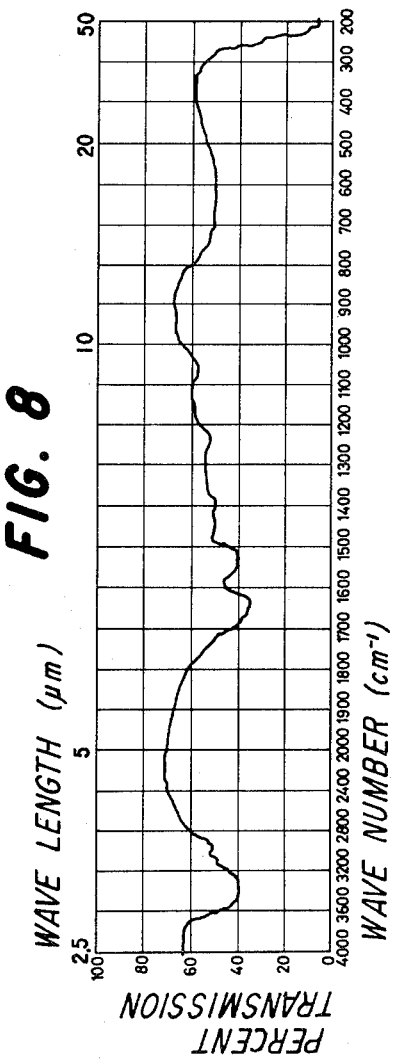

PHARMACEUTICAL COMPOSITION HAVING ANTITUMOR ACTIVITY

SUMMARY OF THE INVENTION

The present invention relates to a pharmaceutical composition formed by an amide bonding between a highly pure antibody to tumour antigen and an antitumour substance.

The first characteristic aspect of the present invention is to provide a pharmaceutical composition which does not cause side effects such as pyrexia and anaphylactic shock when administered.

The second characteristic aspect of the present invention is to provide an extremely pure antibody to tumour antigen, which is suitable for preparation of the above-mentioned pharmaceutical composition.

BACKGROUND OF THE INVENTION

Although recently, several kinds of pharmaceutical composition have been proposed and put into practical use, almost of them exhibit side effects such as leukocytopenia, alopecia and gastrointestinal disturbances. Accordingly, in actual fact, their application is restricted to an extent.

More recently, the application of a substance obtained by chemically bonding an antibody to tumour antigen (hereinafter referred to an anti-tumour-antibody) with an antitumour substance, as an antitumour agent, has been tried. However, since the anti-tumour-antibody used for such a substance is not sufficiently purified, to remove general immunoglobulin and so it could not be recognized as a pure anti-tumour-antibody. Accordingly, in the case where such a substance obtained by bonding such an anti-tumour-antibody with an antitumour substance is administered as an antitumour agent, the occurrence of pyrexia and anaphylactic shock caused by immunoglobulin contained in the above-mentioned anti-tumour-antibody is inevitable.

The inventors taking into consideration of the above-mentioned technical backgrounds have examined the elimination of side effects observed in the use of anti-tumour-antibody and as a result, have confirmed that the extremely pure anti-tumour-antibody is obtained by purifying the immunoglobulin fraction of the antiserum with an affinity-chromatographic technique and that a pharmaceutical composition obtained by bonding the above-mentioned purified antibody to an antitumour substance having at least one amino group or carboxyl group does not exhibit the above-mentioned side effects.

Accordingly, an object of the present invention is to supply a pharmaceutical composition having low cytotoxicity and on the other hand excellent antitumour activity. Also an another object of the present invention is to supply an anti-tumour-antibody with a high purity and a method for preparing the same.

BRIEF EXPLANATION OF DRAWINGS

FIG. 1 of DRAWINGS shows an infrared absorption spectrum of a composition obtained by bonding a purified antisarcoma-180 antibody from a mouse to mitomycin C according to the present invention;

FIG. 2 shows an infrared absorption spectrum of the purified antibody obtained by the purification with affinity-chromatography of an antiserum collected from a male patient suffering from the rectal cancer;

FIG. 3 shows an ultra-violet absorption spectrum of the above-mentioned purified antibody;

FIG. 4 shows an infrared absorption spectrum of a composition obtained by bonding a purified antisarcoma-180 antibody from a mouse to doxorubicin hydrochloride according to the present invention;

FIG. 5 shows an infrared absorption spectrum of a composition obtained by bonding a purified antisarcoma-180 antibody from a rat to chlorambucil according to the present invention;

FIG. 6 shows an infrared absorption spectrum of a composition obtained by bonding a purified antisarcoma-180 antibody from a rat to uramustine according to the present invention;

FIG. 7 shows an infrared absorption spectrum of a composition obtained by bonding a purified antisarcoma-180 antibody from rabbit to cytarabine according to the present invention; and FIG. 8 shows an infrared absorption spectrum of a composition obtained by bonding a purified antisarcoma-180 antibody from a mouse to 5-fluorouracil according to the present invention.

DETAILED DESCRIPTION OF THE INVENTION

The characteristic feature of the present invention resides in that a pharmaceutical composition obtained by bonding a purified antitumour-antibody obtained by purification with affinity-chromatography to an antitumour substance having at least one amino group or carboxyl group is used as an active component of the pharmaceutical composition of the present invention.

The antitumour-antibody used in the present invention is obtained by purifying the immunoglobulin fraction induced by the antigen of the tumours including sarcoma-180, Sato's lung cancer, L-1210 leukemia, P-388 leukemia, Ehrlich's cancer, Yoshida's sarcoma, acute lymphatic leukemia, medullary tumour, or other human cancers with an affinity-chromatographic technique.

The preparation of the antibody itself to the above-mentioned tumour antigen follows the method recorded in "Proceedings of the VIth Annual Meeting of Japan Society of Immunology", page 198 (1976) or the method of Dauphin, M. J. et al. (refer to "J. Immunul.", 113, page 948 (1974)). In the former method, using the Freund's complete ajuvant, tumour cells are subcutaneously injected into experimental animals to immunize them and the antibody is obtained from the immunized animals. In the latter method, a tumour antigen is intraperitoneally injected 3 to 4 times in an animal to immunize the animal and the antibody is obtained from the immunized animal.

In addition, either of the alloantibody and genoantibody may be used in the present invention, however, the use of the alloantibody is preferable.

Hitherto, in order to purify an antibody, the method of, using both the salting-out with ammonium sulfate and the ion-exchange chromatography with DEAE cellulose column, obtaining the immunoglobulin G fraction from an antiserum has been frequently utilized. In the present invention, a specifically purifying procedure is carried out by using affinity-chromatography to selectively obtain only the specific antibody to the tumour cells from the immunoglobulin G fraction obtained by the above-mentioned method. The affinity-chromatography is based on the principle that utilizing a specific affinity between substances of living bodies, for instance, between an enzyme and a substrate or between an antibody and antigen, and then separating one of such pair.

The affinity-chromatography used in the present invention includes (1) a method in which molecules of an antigen, extracted from tumour cells are covalently bonded to a carrier such as agarose gel while using bromocyan and after filling a column with the carrier, a solution of an antibody is passed through the column to bond the antibody to the antigen and then a sufficient amount of a solvent is passed through the column to wash out not-bonded antibody, and a buffer solution at a lower pH is passed through the column to release the bonding between the antibody and the antigen and to eluate the separated antibody, (2) a method in which without using a column, the antibody is made to bond with the antigen by mixing the carrier to which the antigen has been bonded as is described above and a solution of the antibody, and then after washing the carrier particles to remove the not-bonded antibody, the antibody is dissolved out, and (3) a method in which the tumour cells themselves are used instead of the carrier to which the antigen is bonded.

Accordingly, the purified antibody obtained in the present invention with the affinity-chromatography is an antitumourimmunoglobulin with a higher purity than the conventional immunoglobulin fraction, that is, it is a purified antitumour-antibody.

The antitumour substances which are to be bonded by amido bonding with the purified antitumour-antibody obtained as above include the antibiotic substances such as mitomycin C, doxorubicin hydrochloride, bleomycin, daunorubicin, actinomycin D and sarcomycin; the antimetabolitic substances such as cytarabine, 8-azaguanine, 5-fluorouracil, methotrexate and sodium aminopterin; and the alkylating agents such as chlorambucil, melphalane, uramustine, ACNU and cyclophosphamide. Each of the above-mentioned antitumour substances is publicly known and indicated by a trivial name, their structural formulae being described, for instance, in the following literatures:

"Iyakuhin Yōran (Manual of Drugs)", Ed. by Osaka Prefectural Assoc. Hospitals' Pharmacysts.

"Biseibutsuyakuhin Kagaku (Chemistry of Drugs derived from Microorganisms)" Ed. by Ueno, Y. et al.

The above-mentioned antitumour substance is bonded to the above-mentioned antitumour-antibody via the bonding of either the amino group or the carboxyl group in the substance with either the carboxyl group or the amino group in the antibody by bringing the substance into reaction with the antibody under mild conditions. In this case, it is possible to have a more smooth reaction, if necessary, by introducing amino group(s) or carboxyl group(s) into the antitumour substance in advance. The introduction of the amino- or carboxyl group(s) is preferably carried out by making the antitumour substance itself or its salt of sodium, potassium or silver into reaction with a compound represented by the general formula of $X(CH_2)_nCOOH$, wherein X represents an atom of chlorine or bromine and n denotes an integer of 1 to 3 or of $HCl.NH_2(CH_2)_nCOX$, wherein X represents an atom of chlorine or bromine and n denotes an integer of 1 to 3, in a water-soluble solvent, for instance, methanol, ethanol, dimethylsulfoxide or dioxane at a temperature of 0° to 50° C., preferably of 10° to 40° C. for 10 minutes to 72 hours. By recrystallizing the thus obtained reaction product from a solvent such as water, an alcohol, chloroform and dioxane a derivative of the antitumour substance, to which amino group(s) or carboxyl group(s) is(are) introduced is obtained. Chloroacetic acid is preferable as the compound represented by the formula of $X(CH_2)_nCOOH$.

The bonding of the purified antitumour-antibody and an antitumour substance having at least one of amino group or carboxyl group is carried out by dissolving both the two reactants in a water-soluble solvent and adding a carbodiimide as a catalyst to carry out the reaction at a temperature of 0° to 50° C., preferably of 10° to 40° C. for 10 minutes to 8 hours, preferably for 30 minutes to 5 hours and stopping the reaction by the addition of a buffer solution such as acetic acid-sodium acetate.

In the next place, in order to remove the unreacted antitumour substance, the catalyst, components of the buffer solution and salts in the reaction mixture, the reaction mixture is subjected to one of the treatments of dialysis, gelfiltration and ultrafiltration or to a combination of these treatments. The carbodiimide used in the above-mentioned reaction as the catalyst includes 1-ethyl-3-(3-dimethylaminopropyl)-carbodiimide, 1-cyclohexyl-3-(3-morfolinoethyl)-carbodiimide and dicyclohexylcarbodiimide.

In the pharmaceutical composition obtained by the above-mentioned reaction the antibody and the antitumour substance are bonded by(an) amide bond(s), and the molecular ratio of antibody to antitumour substance is 1: 2 to 5 in cases where the antitumour substance is of antibiotic origin and is 1: 1 to 10 in cases where it is of antimetabolitic or alkylating origin.

The followings are the explanation of the toxicological specificity, the pharmacological effects and the preparation of the bonded substance, the pharmaceutical composition of the present invention, having an amide bonding between the above-mentioned antitumour-antibody and the antitumour substance.

The acute toxicity was examined by intravenation of 300 mg of the pharmaceutical composition per kg of a mouse as the experimental animal. Because no death was observed in the group of treated mice within one week after the treatment, it can be said that the pharmaceutical composition has an adaptability as a medicine.

The pharmaceutical composition, as shown by Examples, is effective to several cancerous diseases such as acute leukemia, malignant lymphoma, carcinoma, sarcoma, malignant ciliated epithelioma, acute myelogenous leukemia, melanoma, acute lymphatic leukemia, myeloma, etc.

As for the method for formulating the preparation of the pharmaceutical composition for use as an antitumour drugs and the method of administration thereof, the publicly known methods may be applied. As for the method of administration, oral-, injectional- or rectal administration is mentioned, and as for the form on administration, powder, granule, tablet, injection and suppository are included, however, particularly, the administration by injection is preferable. For the preparation of an injection, water-soluble solvents such as physiological saline solution, sterilized water, Ringer's solution, etc., water-insoluble solvents, isotonication agent, analgesic agent, stabilizing agent, antiseptic, suspending agent, buffering agent, emulsifying agent, etc. are optionally used.

As for an instance, 10 mg of the pharmaceutical composition and 50 mg of mannitol are dissolved in distilled water to be 10 ml of an aqueous solution, and after sterilizing the solution by a conventional method the sterilized solution is introduced into a vial for injection, or the solution is directly freeze-dried to be an injection which is, on application, diluted with an aqueous physiological saline solution.

The pharmaceutical composition may be included in a preparation at a concentration of, generally 0.01 to 90% by weight, preferably 0.1 to 60% by weight.

Although the amount of administration of the pharmaceutical composition depends upon the state of diseases, it is generally 0.11 to 9 g per day per an adult person, preferably 0.1 to 6 g.

In addition, according to the present invention, since the tumourtropy and antitumour activity of the antibody and the antitumour activity of the antitumour substance which is bonded to the antibody are kept within the pharmaceutical composition without having been lost, the permaceutical composition, when administered, arrives at the target site of the tumour effectively and exhibits its antitumour activity. Accordingly, when considered the amount of the pharmaceutical composition as the base, the administration of the pharmaceutical composition containing an amount of the antitumour substance of one tenth to one twentieth of the amount of the administration of the same antitumour substance itself exhibits the same degree of inhibition against the proliferation of the tumour as the administration of the antitumour substance itself, and the degree of side effects due to the antitumour substance contained in the pharmaceutical composition as a component is expected to be only one tenth to one twentieth of the degree of side effects due to the preparation comprising the same antitumour substance. These effects are possibly said to be a synergistic effect of favorable properties of the two components of the pharmaceutical composition.

The followings are the concrete explanation of the method for producing and the pharmacological effectiveness of the antitumour agent of the present invention referring to Examples non-limitative.

EXAMPLE 1

1—1: Preparation and purification of the antibody by utilizing affinity-chromatography (3).

After culturing the cells of ascites-type sarcoma-180 successively cultured using ICR mouse, in an aqueous physiological solution containing mitomycin C at a concentration of 50 microgram/ml for 30 minutes at a temperature of 37° C., the supernatant liquid was removed by centrifugation, and the proliferated cells have washed three times with an aqueous 0.85% physiological saline solution. Freud's complete ajuvant (hereinafter abbreviated as FCA) was admixed with the thus treated cells of sarcoma 180 deprived of its proliferative activity and the mixture was injected subcutaneously into the sole of a rabbit of body weight of 2.9 kg at a rate of $10^8$ cells/animal. The rabbit was immunized by a repeated injection of the cells 2 weeks after the first injection and then the same number of the cells was intravenated to the same rabbit.

After one week of the last injection, the whole blood of the rabbit was collected by a cannula inserted into the carotid artery, and an antiserum was prepared from the blood and purified as follows:

The salted-out fraction formed by the addition of ammonium sulfate in an amount of 20 to 30% by weight of the amount of saturation to 100 ml of the antiserum was collected and re-dissolved in 20 ml of water. The solution was desalted by dialysis against an aqueous 10 mM phosphate buffer solution (hereinafter abbreviated as PBS) at a pH of 7.0 for 72 hours at a temperature of 4° C. (during the procedure, the external dialysis liquid being exchanged every 24 hours). An equal amount of blood cells of a normal ICR mouse, washed 3 times with an aqueous sodium chloride solution was admixed with the desalted solution and the mixture was left to stand for 30 minutes at a temperature of 4° C. for the absorption. Then the mixture was subjected to centrifugation to obtain a supernatant liquid. The above-mentioned procedure was repeated 4 times, the total times of absorption procedure being 5. The thus obtained antibody is called the pre-purification antibody (generally called as IgG). In the next place, the purification was further carried out according to the following method: To the supernatant solution subjected to the absorption, the same amount of the cells of sarcoma-180 was admixed and then the mixture was left to stand for 30 minutes at a temperature of 4° C. to make the antibody against sarcoma-180 bonded to the cells of sarcoma-180 and the supernatant solution was removed by centrifugation. An aqueous glycine-hydrochloric acid buffer solution of pH of 3.0 was added to the precipitate to release the antibody. The mixture was centrifugated to collect the supernatant solution containing the antibody. After adjusting the pH of the supernatant solution nearly to neutral with the addition of aqueous 0.1 N sodium hydroxide solution, the nearly neutralized solution was dialyzed against PBS at a temperature of 4° C. for 24 hours (external dialysis liquid being exchanged every 8 hours). The thus obtained dialyzed solution is an aqueous solution containing the rabbit's anti-sarcoma-180 antibody.

1-2: Cytotoxicity test against tumour cells and normal cells:

Disturbance due to the rabbit's anti-sarcoma-180 immuno-antibody obtained as described above to the cells was tested under the presence of a complement (guinea pig's serum) as follows:

Each 100 microliters of the above-mentioned aqueous solution of the antibody, and of the three diluted solutions of the antibody to 10 times, 100 times and 1,000 times, respectively, was mixed with 100 microliters of the aqueous suspension of cells of sarcoma-180 or of the splenic cells of a normal ICR mouse (either of the suspensions used Eagle's minimum essential medium as a solvent, containing $5 \times 10^6$ cells/ml), and the mixtures were left to stand for 15 minutes at the room temperature. Then, an aliquot of 100 microliters of a 2 times diluted serum of a guinea pig with Eagle's minimum essential medium (hereinafter referred as MEM) (the diluted serum is referred as a complement) was added to each of the above-mentioned mixture, and the final mixtures were incubated for 30 minutes at a temperature of 37° C. After incubation, the incubated medium was centrifugated to collect cell pellets, and after washing the pellets once with MEM, an aqueous trypan-blue solution was added to the pellets to be examined under microscope for the evaluation of mortality of the cells.

The results are shown in Table 1. As is seen in Table 1, when the degree of mortality of the cells (cell-cytotoxicity activity) was classified into 3 levels and indicated by +, ++ and +++ (no death is shown by "—"), it is shown very well that although the antibody taken out after purification of the antiserum by the above-mentioned method showed a cytotoxicity to sarcoma-180 cells not so much different from the toxicity of the antibody taken out without purifying the antiserum, the toxicity of the former to the splenic cells of a normal ICR mouse was extremely low not to have killed them. It shows that the purification of the antiserum was suitable for the purpose of the present invention.

TABLE 1

| Times of dilution of aqueous solution of the antibody | | Mortality of Cells | | | |
|---|---|---|---|---|---|
| | | 1 | 10 | 100 | 1000 |
| Before purification of antiserum by affinity chromatography (3) | Cells of sarcoma-180 | +++ | +++ | + | – |
| | Splenic cells of ICR mouse | ++ | + | – | – |
| After purification of antiserum by affinity chromatography | Cells of sarcoma-180 | +++ | +++ | ++ | – |
| | Splenic cells of ICR mouse | + | – | – | – |
| Control (Eagle' MEM) | Cells of sarcoma-180 | – | – | – | – |
| | Splenic cells of ICR mouse | – | – | – | – |

It is added that the splenic cells of a normal ICR mouse used as the representative of normal cells were obtained by at first after extirpation of the spleen, mincing finely the spleen with a pair of tweezers in Eagle's MEM to pass through a stainless steel netting of 200 mesh, washing the filtrate once with MEM, adding 3 ml of an aqueous tris-(hydroxymethylamino) methane-buffered 0.75% ammonium chloride solution of pH of 7.4 to the washed filtrate to remove the erythrocytes and washing the thus treated filtrate three times with MEM.

1-3: Purification of the antibody by affinity-chromatography:

Since in the method (3) of affinity-chromatography used in 1-1 above-mentioned there are problems in the separation of the pure antibody that the disturbance is still recognized on the mouse's splenic cells, the following purification of the antibody was carried out utilizing a column to which the tumour-antigen is bonded. At first, purification was performed on the antigen itself.

Tumour cells of ascites-type sarcoma-180 which have been successively cultured using ICR mice were freeze-dried and after adding an aqueous 5 mM potassium phosphate buffer solution of pH of 7.4 the antigen was extracted from the cells for 20 hours. A supernatant solution was collected by centrifugating the mixture for 10 minutes at 65,000 G. The supernatant solution was further centrifugated for 30 minutes at 180,000 G and the thus obtained supernatant was dialyzed against distilled water for 70 hours at a temperature of 4° C. (during the dialysis, the external liquid was exchanged every 24 hours). The dialyzate was further centrifugated at 65,000 G to remove the precipitate, and after adding ammonium sulfate into the thus obtained supernatant solution to make its concentration 2 M, the solution was centrifugated for 10 minutes at 65,000 G to collect the precipitate. The precipitate was dissolved into distilled water, and the solution was dialyzed against distilled water for 72 hours (during the dialysis, the external liquid was exchanged every 24 hours).

The thus obtained antigen of sarcoma-180 was used for preparing the column for affinity-chromatography as follows:

At first, to an agarose gel (Sepharose 4B, product of Pharmacia Japan Co., Ltd.) swollen with water to be 20 ml, the same volume of an aqueous solution of bromocyan at 1 g/ml was added, and after making reaction for 8 minutes while maintaining the pH of the reaction mixture at 11.0 the mixture was filtered with a glass filter to collect the precipitate which was washed on the filter with ice-cooled distilled water and an ice-cooled aqueous 0.5 M sodium hydrogen carbonate solution. Just after the washing, the precipitate was suspended into an aqueous 0.1 M sodium hydrogen carbonate solution. The above-mentioned solution of the purified antigen was added to the suspension and the mixture was stirred overnight to make reaction. The product was filtered with a glass filter and washed with, at first, an aqueous 0.1 M sodium hydrogen carbonate solution, then with distilled water and at last with an aqueous phosphate buffer solution of sodium chloride (0.85%, pH of 7.0). The thus washed reaction product was packed into a glass tube of 13 mm in internal diameter and 15 cm in length to be the column for affinity chromatography. Three milliliters of the solution of antibody (IgG) prepared by the procedure of above-mentioned 1-1 except for the step of bonding with the cells of sarcoma-180 were poured into the column and then an aqueous 5 mM phosphate buffer solution of sodium chloride (0.85%, pH of 7.0) was flowed into the column until protein became undetectable in the effluent, and then an aqueous 0.5 M sodium chloride solution added with an aqueous 50 mM glycine hydrochloride buffer solution was flowed into the column to collect the fraction as the eluate. The eluate was rapidly neutralized with sodium hydrogen carbonate and the neutralizate was dialyzed against an aqueous phosphate buffer solution of sodium chloride (0.85%, pH of 7.0) for 72 hours (the external liquid was exchanged every 24 hours). The dialyzate thus obtained was an aqueous solution of a purified antibody against sarcoma-180 by column-affinity-chromatography.

1-4: Cytotoxicity test against tumour cells and normal cells:

Cytotoxicity due to the rabbit's anti-sarcoma-180 antibody obtained in 1-3 was examined by the method described in 1-2 on the tumour cells and normal cells. The results are shown in Table 2.

TABLE 2

| Times of dilution of the antibody | | Mortality of Cells | | | |
|---|---|---|---|---|---|
| | | 1 | 10 | 100 | 1000 |
| Solution of the antibody after purification by column-affinity chromatography (3) | Cells of sarcoma-180 | +++ | +++ | ++ | – |
| | Cells of spleen of mouse | + | – | – | – |
| Solution of the antibody after purification by column-affinity chromatography (1) | Cells of sarcoma-180 | +++ | +++ | ++ | + |
| | Cells of spleen of mouse | – | – | – | – |
| Control (Eagle' MEM, only) | Cells, sarcoma | – | | | |
| | Cells, splenic | – | | | |

The tabulated results in Table 2 show the reduction of toxicity to the splenic cells and the accentuation of the activity to the cells of sarcoma-180 of the antibody owing to the purification of the antibody by affinity-chromatography (1), that is, show the excellent purification of the antibody by affinity-chromatography (1).

1-5: Bonding between the anti-sarcoma-180 antibody and an antitumour substance:

Each anti-sarcoma-180 antibody of rabbit prepared according to the method of 1-1 and 1-3 mentioned before and purified by each of the methods of purification mentioned before was made to react with each of the antitumour substances such as mitomycin C, daunorubicin, bleomycin, actinomycin D, sarcomycin and doxorubicin hydrochloride to produce each substance. As an example, the reaction of the antibody prepared in 1-1 and mitomycin C is described as follows:

To an aqueous solution containing the purified rabbit's anti-sarcoma-180 antibody at a concentration of 10.4 mg/ml, 13.0 mg of mitomycin C was added, and under agitation while adjusting the pH of the solution to 4.75, 3.7 mg of 1-ethyl-3-(3-dimethylaminopropyl) carbodiimide hydrochloride was added to make react for the period indicated in Table 3 and the reaction was stopped by the addition of 2 ml of an aqueous acetic acid-sodium acetate buffer solution of pH of 4.70. After dialyzing the reaction mixture against 5 liter of distilled water at a temperature of 4° C. for 72 hours (during the dialysis, the external liquid was exchanged 3 times), the inner dialysis liquid was condensed and flowed into a column of 1.5 cm in diameter and 55 cm in height packed with a dextran derivative (Sephadex G-25, prepared by Farmacia Japan Co.) to have low-molecular substances in the reaction mixture completely adsorbed onto the column and the eluate was freeze-dried at a temperature of −20° C. to obtain the product. The amount of mitomycin C bonded to the antibody was determined as time passed by using ultraviolet absorption spectroscopy, the results being shown in Table 3.

TABLE 3

Amounts of bonded Mitomycin C to the Antibody

| Reaction time (minute) | Amount of Mitomycin C/antibody (microgram/mg) |
| --- | --- |
| 10 | 4.2 |
| 30 | 8.4 |
| 60 | 10.0 |

One of the pharmaceutical composition is a modified protein of a molecular weight of about 150,000, soluble in water and insoluble in organic solvents such as benzene, acetone, methanol, etc. This compound shows an infrared absorption spectrum as shown in FIG. 1. In an ultraviolet absorption spectrum, the specific absorption peaks at 280 and 360 nm were seen.

According to the above-mentioned procedures, the purified rabbit's anti-sarcoma-180 antigen (10 mg) was made to react with each of doxorubicin hydrochloride, daunorubicin and actinomycin D to obtain each of the bonded compounds of about 7 mg. The amounts of doxorubicin hydrochloride bonded to 1 mg of the antibody protein were 4.1 microgram and 9.0 microgram, respectively for the time of reaction of 10 and 30 minutes. The same results were obtained by the use of IgG antibody.

In the next place, the rabbit's purified anti-sarcoma-180 antibody was made to react with mitomycin C under the same conditions as those above-mentioned to obtain a compound having almost the same physico-chemical properties as those of the above-mentioned compound. Compounds bonded respectively to daunorubicin, bleomycin, actinomycin D, sarcomycin and doxorubicin hydrochloride were synthesized according to the above-mentioned method under the same conditions as above.

EXAMPLE 2

2-1: Preparation of an antibody to tumour cells and purification of the same.

Ascites-type sarcoma-180 cells successively cultured using ICR mice and deprived of their proliferative activity by mitomycin C were intraperitoneally injected into an ICR mouse once per week at a rate of $10^7$ cells/animal in total 4 times and on the 7th day of the last injection, the blood was collected from the mouse's abdominal large vein on its laparatomy under anesthesia, and an antiserum was prepared from the blood in an amount of 53 ml from 100 animals. The collection of the antibody from the antiserum and the purification of the antibody were performed following 1-1 and the procedure was stopped after absorption by mouse's erythrocytes.

2-2: Purification of an antibody by affinity-chromatography:

To 30 g of the freeze-dried ascites-type sarcoma-180 cells successively cultured by using ICR mice, an aqueous solution 3MKCl solution buffered with an aqueous 5 mM potassium phosphate buffer solution of pH of 7.4 was added to extract the antigen for 20 hours. The extract was centrifugated for 10 minutes at 65,000 G to collect the supernatant liquid and the supernatant liquid was further centrifugated for 30 minutes at 180,000 G to collect the supernatant liquid. It was dialyzed against distilled water at a temperature of 4° C. for 72 hours (during the dialysis, the external liquid was exchanged every 24 hours.)

The affinity-chromatography of the thus obtained antigen of sarcoma-180 was carried out as follows:

Twenty milliliters of water-swollen agarose gel (Sepharose 4B, Farmacia Japan Co., Ltd.) were mixed with 20 ml of an aqueous bromocyan solution at a concentration 1 g/ml while keeping the pH of the mixture at 11.0 for 8 minutes to bring it into reaction, and the reaction mixture was filtered by a glass filter. The separated filtrate was washed with ice-cooled distilled water and ice-cooled aqueous 0.5 M sodium hydrogen carbonate solution on the filter and at once it was suspended in an aqueous 0.1 M sodium hydrogen carbonate solution and the above-mentioned purified antigen solution was added to the suspension while stirring overnight at the room temperature to make them react. The product was filtered by a glass filter and washed with at first an aqueous 0.1 M sodium hydrogen carbonate solution, then distilled water and at last with an aqueous phosphate buffer solution of sodium chloride (0.85%, pH of 7.0). The washed product was packed into a glass tube of 13 mm in inner diameter and 15 cm in height to be a column for affinity-chromatography.

Three milliliters of the antiserum made by the procedure in 2-1 described before (including an antibody) was flowed into the affinity-chromatographic column, and then an aqueous 5 mM phosphate buffer solution of sodium chloride (0.85%, pH of 7.0) was flowed into the column until protein became undetectable in the effluent, and an aqueous 0.5 M sodium chloride solution added with an aqueous 5 mM glycine-hydrochloric acid buffer solution (pH of 4.0) was flowed into the column to collect the eluate fraction. The eluate fraction, after neutralized with sodium hydrogen carbonate, was at once dialyzed against an aqueous phosphate buffer solution of sodium chloride (0.85%, pH of 7.0) for 72 hours (during dialysis, the external liquid was exchanged every 24 hours). The aqueous solution of an antibody to sarcoma-180 purified by the use of affinity-chromatography was thus obtained.

2-3: Cytotoxicity test against tumour cells and normal cells:

Cytotoxicity due to the mouse's sarcoma-180 antibody was examined by the method as in Example 1, the results being shown in Table 4.

TABLE 4

| Times of dilution of the antibody | | Mortality of Cells | | | |
|---|---|---|---|---|---|
| | | 1 | 10 | 100 | 1000 |
| Solution of antibody before purification by affinity chromatography (1) (2-1) | Cells of sarcoma-180 | +++ | ++ | − | − |
| | Cells of spleen of mouse | − | − | − | − |
| Solution of antibody after purification by affinity chromatography (1) (2-2) | Cells of sarcoma-180 | +++ | +++ | ++ | + |
| | Cells of spleen of mouse | − | − | − | − |
| Control (Eagle's MEM) | Cells of sarcoma-180 | − | | | |
| | Cells of spleen of mouse | − | | | |

As is seen in Table 4, the activity to sarcoma-180 cells has been raised remarkably by affinity-chromatography as mentioned before.

2-4: Bonding of mouse's anti-sarcoma-180 antibody with an antitumour substance:

Mouse's anti-sarcoma-180 antibodies obtained by 2-1 and 2-2, respectively were bonded to mytomycin C by the method described in 1-5, the two substances being bonded with an amido bonding. By the same method, each of doxorubicin hydrochloride, bleomycin, daunorubicin, actinomycin D and sarcomycin was bonded to the antibody with an amido bonding. The pharmaceutical compound obtained as above showed almost the same physicochemical properties as the corresponding compound obtained in 1-5. In Example 3, the representative compounds obtained in 1-5 and 2-4, respectively were examined on their antitumour activity.

EXAMPLE 3

Antitumour activity of the pharmaceutical composition against solid-type sarcoma-180;

Cells of mouse's sarcoma-180 successively cultured by using ICR mice were transplanted subcutaneously to axilla of each group of ICR mouse, the group being consisted of 10 animals, at a rate of $1 \times 10^6$ cells/animal. From after 24 hours of the transplantation, intraperitoneal injection of each of the following agents was carried out once every other day in total ten times and after 5 days of the last injection all the mice were sacrificed to extirpate the tumour. The averaged weight of the tumours $(\overline{T})$ was compared so that $(\overline{C})$ of 10 mice administered with an aqueous physiological saline solution instead of the agent in the following formula to show the rate of inhibiting the proliferation of the tumour (sarcoma-180) by the agent:

$$(1 - \overline{T}/\overline{C}) \times 100$$

in Tables 5, 6, 7 and 8. The above-mentioned agents were: (1) antibodies, (2) commercial antitumour drugs, (3) pharmaceutical composition of rabbit's anti-sarcoma-180 antibody bound to each of commercial antitumour drugs and (4) pharmaceutical composition of mouse's anti-sarcoma-180 antibody bound to each of commercial antitumour drugs. Table 5 shows pharmaceutical composition synthesized with mitomycin C, Table 6 shows pharmaceutical composition synthesized with bleomycin, Table 7 shows pharmaceutical composition synthesized with doxorubicin and Table 8 shows the results of administration of the antibodies.

TABLE 5

Mitomycin and pharmaceutical composition of Antibodies bound to Mitomycin

| | Agent | Amount of administration (mg/kg) | | Effect of inhibiting Proliferation (%) |
|---|---|---|---|---|
| | | Total | *MMC | |
| | mitomycin C | 1 | 1 | 40 |
| Present Composition | Rabbit's antibody | 5 | 0.05 | 32 |
| | Rabbit's antibody **A₃ | 5 | 0.05 | 37 |
| | Rabbit's antibody **A₁ | 5 | 0.05 | 40 |
| | Mouse's antibody | 5 | 0.05 | 39 |
| | Mouse's antibody **A₁ | 5 | 0.05 | 40 |

Note:
*MMC: Mitomycin, and
A₁ or A₃: antibody purified by affinity-chromatography (1) or (3)

TABLE 6

Bleomycin and pharmaceutical composition of Antibodies bound to Bleomycin

| | Agent | Amount of administration (mg/kg) | | Effect of inhibiting proliferation (%) |
|---|---|---|---|---|
| | | Total | Bleomycin | |
| | Bleomycin C | 0.5 | 0.5 | 45 |
| Present Composition | Rabbit's antibody | 5 | 0.05 | 36 |
| | Rabbit's antibody **A₃ | 5 | 0.05 | 42 |
| | Rabbit's antibody **A₁ | 5 | 0.05 | 45 |
| | Mouse's antibody | 5 | 0.05 | 44 |
| | Mouse's antibody **A₁ | 5 | 0.05 | 45 |

TABLE 7

Doxorubicin HCl and pharmaceutical composition of Antibodies bound to Doxorubicin HCl

| | Agent | Amount of administration (mg/kg) | | Effect of inhibiting proliferation (%) |
|---|---|---|---|---|
| | | Total | **Do. | |
| | Doxorubicin hydrochloride | 2 | 2 | 50 |
| Present Compound | Rabbit's antibody | 20 | 0.2 | 40 |
| | Rabbit's antibody **A₃ | 20 | 0.2 | 47 |
| | Rabbit's antibody **A | 20 | 0.2 | 50 |
| | Mouse's antibody | 20 | 0.2 | 49 |
| | Mouse's antibody **A | 20 | 0.2 | 50 |

Note: **Do.: Doxorubicin hydrochloride

TABLE 8

| Antibody | | Antibodies Amount of administration (mg/kg) | Effect of inhibiting Proliferation (%) |
|---|---|---|---|
| Rabbit | | 5 | 4 |
| | **A$_3$ | 5 | 5 |
| | **A$_1$ | 5 | 5 |
| Rabbit | | 20 | 5 |
| | **A$_3$ | 20 | 5 |
| | **A$_1$ | 20 | 5 |
| Mouse | | 5 | 6 |
| | **A$_1$ | 5 | 7 |
| Mouse | | 20 | 7 |
| | **A$_1$ | 20 | 7 |

A$_1$ or A$_3$: antibody purified by affinity chromatography (1) or (3)

As are seen in Tables 5 to 7, the rate of inhibition of proliferation of sarcoma-180 of the pharmaceutical composition is, in actual state, nearly the same as that of commercial antitumour agents at a dose rate of 5 to 10 times of the dose rate of commercial antitumour agents. This fact shows that the antitumour activity of the antibody itself does not appear substantially and it is really natural. The characteristic of the pharmaceutical composition becomes clear when the amount of administration of commercial antitumour agent is compared to the amount of commercial antitumour agent as one of the components of the pharmaceutical composition. That is, although the amount of the latter is only one tenth or one twentieth of that of the former, the inhibiting effects are almost the same in both cases. The above-mentioned fact is the reflection that the antibody which is one of the components of the pharmaceutical composition well brings the small amount of commercial antitumour agent which is also one of the components of the pharmaceutical composition to the tumour site, the fact realizing the idea of the present invention.

The pharmaceutical composition owing to the above-mentioned function while reducing the amount of administration of the commercial antitumour agent which originally has an extremely high side effects to one tenth to one twentieth of the customary amount of administration, exhibits the same degree of tumour-inhibiting activity.

In addition, it should be noticed that although the origin of the antibody has no relationship to the rate of inhibition of the proliferation of the tumour, when the know compound produced by bonding the antibody prepared by using a rabbit and ordinarily purified to a commercial antitumour substance was administered to 10 mice, about 3 animals showed a general spasm and stiffening, one of the signs of anaphylactic shock, while the administration of the pharmaceutical composition produced by bonding the antibody purified by affinity-chromatography to the antitumour substance only caused a very much reduced occurrence of such an anaphylactic shock. Originally the compound prepared by bonding the antibody derived from mouse and purified by ordinary method to the antitumour substance caused the anaphylactic shock extremely rarely, but when the antibody was further purified by affinity-chromatography, anaphylactic shock was never observed.

EXAMPLE 4

4-1: Preparation of an antibody and purification thereof by using affinity-chromatography Cells of Yoshida's sarcoma successively cultured using Donryu rats were suspended in an aqueous physiological saline solution and after adding mitomycin C (50 microgram/ml) to the suspension, the mixture was incubated for 30 minutes at a temperature of 37° C. and centrifugated to remove the supernatant liquide. The cells were washed three times with an aqueous 0.85% physiological saline solution. Freund's complete ajuvant (hereinafter abbreviated as FCA) was admixed with the cells of Yoshida's sarcoma thus deprived of proliferative activity, and the mixture was subcutaneously injected into the sole of a rabbit of a body weight of 2.9 kg. at a rate of $10^8$ cells/animal. After 2 weeks of the first injection, the second injection of the cells was carried out on the same rabbit with the similar method to immunize the rabbit and after two week of the second injection, the same cells were intravenated into the same rabbit. After one week of the last injection, the whole blood was collected from the rabbit via the canula inserted into the caroted artery. The antiserum prepared from the blood was purified as follows: That is, to 100 ml of the antiserum an amount of ammonium sulfate corresponding to 20 to 30% by weight of saturation was admixed to effect the salting out. The salted-out fraction was re-dissolved into 20 ml of water, and the thus formed solution was dialyzed against an aqueous 10 mM phosphate buffer solution of sodium chloride (hereinafter referred as PBS) of pH of 7.0 at a temperature of 4° C. for 72 hours (during the dialysis, the external liquid was exchanged every 24 hours). An equal amount of erythrocytes of a normal Donryu rat washed three times with an aqueous sodium chloride solution was admixed with the dialyzate and after leaving to stand for 30 minutes at a temperature of 4° C. the mixture for absorption, it was centrifugated to obtain a supernatant liquid. The above-mentioned procedure of absorption was repeated 4 times, the total times of absorption being 5 times. The thus obtained antibody is called as the pre-purification antibody (commonly called as IgG).

In the next place, the IgG was further purified by the following method: That is, to the supernatant liquid subjected to the absorption five times, an equal amount of the cells of Yoshida's sarcoma was admixed, and the mixture was left to stand for 30 minutes at a temperature of 4° C. to bond the antibody against Yoshida's sarcoma to the cells of Yoshida's sarcoma and then the mixture was centrifugated to remove the supernatant liquid. To the precipitate, an aqueous glycine hydrochloride buffer solution of pH of 3.0 was added to release the antibody. This mixture was then centrifugated to collect the supernatant liquid containing the antibody and the supernatant liquid was treated with an aqueous 0.1 M sodium hydroxide solution to nearly neutral and dialyzed against PBS for 24 hours at a temperature of 4° C. (the external dialysis liquid was exchanged every 8 hours). The thus obtained dialyzate is an aqueous solution of rabbit's anti-Yoshida's sarcoma immuno-antibody.

4-2: Cytotoxicity test against tumour cells and normal cells:

Cytotoxicity due to the rabbit's anti-Yoshida's sarcoma immuno-antibody against cells in the presence of a complement (serum of a guinea pig) was examined as follows: the above-mentioned aqueous solution of the antibody, its 10 times-diluted solution, its 100 times-diluted solution and its 1,000 times-diluted solution were respectively mixed with a suspension of Yoshida's sarcoma cells or a suspension of the splenic cells of a normal Donryu rat (both suspention used Eagle's MEM as a medium and the concentration of the cells was $5 \times 10^6$ cells/ml) at a ratio of 100 microliters: 100 microliters and the mixture was left to stand for 15 minutes to have the antibody absorbed to the cells. And 100 microliters of the serum of a guinea pig diluted with Eagle's MEM to 2 times (the diluted serum is called as a complement) was added to the above-mentioned mixture, and the final mixture was incubated for 30 minutes at a temperature of 37° C. and then centrifuged. The thus obtained precipitate was washed once with Eagle's MEM and after adding the trypane-blue solution the mortality of the cells in the washed and stained precipitate was observed microscopically.

The results of the test are shown in Table 9. As is seen in Table 9, when the mortality of the cells (cell disturbance activity) was classified into 3 levels, and indicated by +, ++ and +++ (no death was indicated by "—"), it was observed that although the toxicity of the antibody taken out after purification of the antiserum to the cells of Yoshida's sarcoma was not so much different from the toxicity of the antibody taken out without purification of the antiserum, the former's toxicity of the splenic cells of a normal Donryu rat was extremely low not to kill the rats. This fact indicates that the purification of the antiserum was suitable for the purpose of the present invention.

TABLE 9

| Times of dilution of aqueous solution of antibody | | 1 | 10 | 100 | 1000 |
|---|---|---|---|---|---|
| Solution of antibody before purification by affinity chromatography (3) | Cells of Yoshida's sarcoma | +++ | +++ | + | — |
| | Cells of spleen of rat | ++ | + | — | — |
| Solution of antibody after purification by affinity chromatography (3) | Cells of Yoshida's sarcoma | +++ | +++ | ++ | — |
| | Cells of spleen of rat | + | — | — | — |
| Control (Eagle's MEM) | Cells of Yoshida's sarcoma | — | — | — | — |
| | Cells of spleen of rat | — | — | — | — |

In addition, the splenic cells of Donryu rat used as the representative of the normal cells were obtained by after extirpation of the spleen, finely crushing the spleen with a pair of tweezers in Eagle's MEM, letting the fragments pass a stainless steel netting of 200 mesh through, washing the passed fragments once with Eagle's MEM, mixing with 30 ml of an aqueous tris-(hydroxylmethylamino) methane buffered 0.75% ammonium chloride solution of pH of 7.4 to destract the erythrocytes in the specimen and washing the fragments three times with Eagle's MEM.

4-3: Purification of an antibody by affinity-chromatography (1):

The following purification of an antibody was carried out by affinity-chromatography using a column with a carrier to which a tumour antigen has been bonded. At first, the antigen itself was purified as follows: That is, the tumour cells of Yoshida's sarcoma successively cultured using Donryu rats were freeze-dried, and to 30 g of this cells an aqueous solution of 3 M KCl buffered with an aqueous 5 mM potassium phosphate buffer solution (pH: 7.4) was added to extract the antigen for 20 hours, and the extract-liquid was centrifugated for 10 minutes at 65,000 G to collect the supernatant liquid and the supernatant liquid was further centrifugated for 30 minutes at 180,000 G to collect the supernatant liquid, which was dialyzed for 70 hours at a temperature of 4° C. (during the dialysis, the external liquid was exchanged every 24 hours). The dialyzate was further centrifugated at 65,000 G to remove the precipitate, and after adding ammonium sulfate to the supernatant liquid to make the concentration to 2 M, the mixture was centrifugated for 10 minutes at 65,000 G to collect the precipitate, which was dissolved into distilled water, and the solution was dialyzed against distilled water for 72 hours (during dialysis, the external liquid was exchanged every 24 hours).

Using the thus obtained antigen of Yoshida's sarcoma, the column for affinity-chromatography was prepared as follows:

To 20 ml of water-swollen agarose gel (Sepharose 4H, made by Farmacia Japan Co., Ltd.) 20 ml of an aqueous bromocyan solution of a concentration of 1 g/ml were added and while keeping the pH at 11.0 the mixture was left to stand for 8 minutes to react each other and the reaction mixture was filtered with a glass filter. The precipitate left on the filter was washed with ice-cooled distilled water and then with ice-cooled aqueous 0.5 M sodium hydrogen carbonate solution followed by dispersing the washed precipitate into an aqueous 0.1 M sodium hydrogen carbonate solution.

The above-mentioned aqueous solution of the purified antigen was added to the dispersion to make the two components react by stirring overnight at the room temperature. The product was filtered with a glass filter and washed at first with an aqueous 0.1 M sodium hydrogen carbonate solution, then with distilled water and at last with an aqueous phosphate buffer solution of sodium chloride (0.85%, pH of 7.0).

The thus washed reaction product was packed in a glass tube of 13 mm in diameter and 15 cm in height to be a column for affinity-chromatography. Into this column, 3 ml of the solution of antibody (IgG) prepared by the procedure of 4-1 above-mentioned (except for the step of bonding with the cells of Yoshida's sarcoma) was flowed and then an aqueous 5 mM phosphate buffer solution of sodium chloride (0.85%, pH of 7.0) was introduced into the column until protein became undetectable in the effluent. Then, an aqueous 0.5 M sodium chloride solution added with an aqueous 50 mM glycine-hydrochloric acid buffer solution (pH of 4.0) was introduced into the column to collect the effluent fraction, which was at once neutralized with sodium hydrogen carbonate and the neutralizate was dialyzed against an aqueous phosphoric acid buffer solution of sodium chloride (0.85%, pH of 7.0) for 72 hours (during the dialysis the external liquid was exchanged every 24 hours). Thus, the aqueous solution of the purified antibody by column affinity-chromatography against Yoshida's sarcoma was obtained.

4-4: Cytotoxicity test against the tumour cells and the normal cells

Cytotoxicity due to the Yoshida's sarcoma-immuno antibody obtained in 4-3 described above was examined by the same method as in 4-2, the results being shown in Table 10.

TABLE 10

| Times of dilution of the antibody | | 1 | 10 | 100 | 1000 |
|---|---|---|---|---|---|
| Solution of antibody after purification with affinity chromatography (3) | Cells of Yoshida's sarcoma | +++ | +++ | ++ | − |
| | Cells of spleen of rat | + | − | − | − |
| Solution of antibody after purification with affinity chromatography (1) | Cells of Yoshida's sarcoma | +++ | +++ | ++ | + |
| | Cells of spleen of rat | − | − | − | − |
| Control (Eagle's MEM) | Cells of Yoshida's sarcoma | − | | | |
| | Cells of spleen of rat | − | | | |

The results show that the activity of the antibody to cells of Yoshida's sarcoma was raised remarkably, however that of the antibody to the splenic cells of rat was reduced by the purification with column affinity chromatography, and that the purification with affinity chromatography is excellent.

4-5: Bonding of anti Yoshida's antibody to an antitumour alkylating agent

Rabbit's anti-Yoshida's sarcoma antibodies prepared and purified in the above-mentioned 4-1 and 4-3 were made to react to one of the commercialized antitumour agents, chlorambucil, melphalan (phenyl alanine mustard), ACNU, uramustine and cyclophosphamide to synthesize each of bonded compounds. The followings are the description of the synthetic examples:

SYNTHETIC EXAMPLE 1

Reaction of the antibody with chlorambucil.

To 10 ml of an aqueous solution containing the purified rabbit's antibody against Yoshida's sarcoma obtained in 4-1 at a rate of 10.0 mg/ml, 40 mg of chlorambucil was added and under agitation while adjusting the pH of the solution at 4.75 with hydrochloric acid, 25.2 mg of 1-ethyl-3-(3-dimethylaminopropyl) carbodiimide hydrochloride was added to the mixture to perform a reaction for 40 minutes. The reaction was stopped by adding 20 ml of an aqueous acetic acid-sodium acetate buffer solution at pH of 4.75.

In the next place, the reaction mixture was dialyzed against 5 liters of distilled water for 72 hours at a temperature of 4° C. (during the dialysis, the external liquid was exchanged three times). After condensing the internal dialysis liquid, the condensate was passed through a column of 3 cm in diameter and 65 cm in height packed with a dextrin derivative (Sephadex G-200, made by Farmacia Japan Co., Ltd.) to completely separate the high molecular weight substances and the low-molecular weight substances in the solution. The effluent from the column was ultracentrifugated for 60 minutes at 40,000 G, and the supernatant liquid was freeze-dried at −20° C. to obtain the object substance. The protein content of the product was determined by Copper-Folin's method using albumin as the standard, and the bonded amount of the alkylating agent was determined by the method of Epstein (Epstein, J. Anal. Chem., 27, 1423 (1955)). The results showed that in the obtained pharmaceutical composition, 10 micrograms of chlorambucil bonded to 1 mg of the antibody.

SYNTHETIC EXAMPLE 2

Reaction of the antibody with melphalan.

In the same manner as in Synthetic Example 1, however, using the same amount of melphalan instead of chlorambucil in Synthetic Example 1, and further using 5 liters of PBS instead of distilled water in dialysis in Synthetic Example 1, the purified rabbit's antibody was bonded to melphalan to obtain a pharmaceutical composition in which 10 micrograms of melphalan bonded to 1 mg of the antibody.

SYNTHETIC EXAMPLE 3

Reaction of the antibody with uramustine.

In the same manner as in Synthetic Example 1, however, using 40 mg of uramustine instead of chlorambucin of Synthetic Example 1, the purified rabbit's antibody was made to react with uramustine. However, it was found that uramustine did not bonded substantially to the antibody. Then, chloroacetic acid was made to react to uramustine to raise the reactivity as follows:

To 10 ml of methanol, 500 mg of uramustine and 139 mg of potassium methoxide were dissolved, and 188 mg of chloroacetic acid was added to the solution followed by agitation for 60 minutes at the room temperature. After the reaction was over, the reaction mixture was condensed under reduced pressure. The residue was recrystallized from methanol and chloroform to obtain 215 mg (yield of 35%) of crystals, of which the following structure of an uramustine derivative was confirmed by analyses:

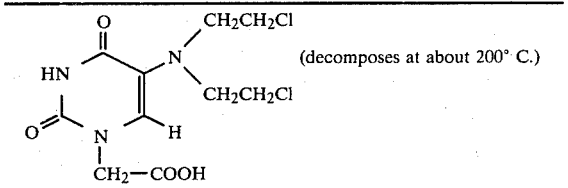

(decomposes at about 200° C.)

| Elementary analysis: | C % | H % | N % |
|---|---|---|---|
| Found: | 38.50 | 4.00 | 13.30 |
| Calcd. as $C_9H_{13}N_3O_4Cl_2$ | 38.70 | 4.19 | 13.54 |

In the next place, the thus obtained derivative of uramustine was made to react with the rabbit's antibody against Yoshida's sarcoma obtained in 4-1 in the same manner as in Synthetic Example 1 to obtain the object pharmaceutical composition in which 10 micrograms of uramustine bonded to 1 mg of the antibody.

SYNTHETIC EXAMPLE 4

Reaction of the antibody with a derivative of melphalan.

At first a derivative of melphalan was synthesized from melphalan as follows:

Into 10 ml of dimethylsulfoxide, 200 mg of silver salt of melphalan were dissolved, and 100 mg of chloroacetic acid were added to the solution followed by the agitation for 64 hours while shading light. After removing the precipitate of the reaction mixture, dimethylsulfoxide and chloroacetic acid were distilled off under reduced pressure on a water bath at a temperature of 80° C.

On adding water to the residue and cooling the mixture, white crystals deposited. The deposited crystals were dried under reduced pressure. The thus obtained derivative of melphalan (yield of 40%) was used in the reaction with the antibody obtained in 4-1 by the same procedure in Synthetic Example 2 to make a pharmaceutical composition in which 16 microgram of the derivative of melphalan bonded to 1 mg of the antibody.

SYNTHETIC EXAMPLE 5

The rabbit's antibody against Yoshida's sarcoma, obtained and purified in 4-3 was made to react with each of the following compounds in the same manner as in Synthetic Example 1: chlorambucil, melphalan, a derivative of melphalan (refer to Synthetic Example 4) and a derivative of uramustine (refer to Synthetic Example 3).

The thus synthesized pharmaceutical composition were almost the same as the pharmaceutical composition obtained in the above-mentioned Synthetic Examples.

EXAMPLE 5

5-1: Preparation and purification of an antibody against tumour cells.

Cells of ascites-type of Yoshida's sarcoma successively cultured using Donryu rats were transplanted once a week into the abdominal cavity of a Donryu rat in total of 4 times, and after 7 days of the fourth transplantation the blood was collected from the abdominal large vein of the rat subjected to laparotomy under anesthesia. The antiserum containing the antibody was prepared from the blood, the amount being 70 ml from 100 rats. The preparation of the antibody from the antiserum and the purification thereof were performed in the same manner as is 4-1, however, the procedure was stopped after absorption with rat's erythrocytes.

5-2: Purification of the antibody by affinity-chromatography (1).

Into 30 g of freeze-dried cells of Yoshida's sarcoma successively cultured by using Donryu rats, an aqueous solution 3 M KCl solution buffered with an aqueous 5 mM potassium phosphate buffer solution at pH of 7.4 was added to effect the extraction of the antigen for 20 hours. The extract liquid was centrifuged for 10 minutes at 65,000 G to collect the supernatant liquid, which was further centrifuged for 30 minutes at 180,000 G to collect the supernatant liquid. The liquid was dialyzed at a temperature of 4° C. for 72 hours against distilled water (during the dialysis, the external liquid was exchanged every 24 hours).

The procedures of affinity-chromatograhy performed on the thus obtained antigen of Yoshida's sarcoma was quite the same as the procedures performed on the antigen of sarcoma-180 in 1-3 of Example 1 (1-3).

5-3: Disturbance test against tumour cells and normal cells.

The disturbance due to the rat's antibody to Yoshida's sarcoma was examined by the same method as in Example 4, the results being shown in Table 11.

TABLE 11

| Times of dilution of aqueous solution of the antibody | Mortality of Cells | 1 | 10 | 100 | 1000 |
|---|---|---|---|---|---|
| Antibody before purification by affinity chromatography (1) | Cells of Yoshida's sarcoma | +++ | ++ | — | — |
| | Splenic cells of rat | — | — | — | — |

TABLE 11-continued

| Times of dilution of aqueous solution of the antibody | Mortality of Cells | 1 | 10 | 100 | 1000 |
|---|---|---|---|---|---|
| Antibody after purification by affinity chromatography (1) | Cells of Yoshida's sarcoma | +++ | +++ | ++ | + |
| | Splenic cells of rat | — | — | — | — |
| Control (Eagle's MEM) | Cells of Yoshida's sarcoma | — | — | — | — |
| | Splenic cells of rat | — | — | — | — |

As is seen in Table 11, the activity of the antibody against the cells of Yoshida's sarcoma has been remarkably raised by affinity-chromatography (1) as were in the preceeding Examples.

5-4: Bonding the rat's antibody against Yoshida's sarcoma to antitumour substances.

The rat's antibodies against Yoshida's sarcoma obtained by the procedures in 5-1 and 5-2 were bonded respectively to chlorambucil by the method quite the same as described in 4-5 to obtain pharmaceutical composition having an amide rinkage between the two components.

By applying the same method to melphalan, a derivative of melphalan and a derivative of uramustine, respectively, each product having a bonding between the antibody and each of the above-mentioned pharmaceutical composition with an amide linkage was obtained.

All of the thus obtained pharmaceutical composition showed almost the same physicochemical properties as those of the corresponding pharmaceutical composition obtained by the procedures in the above-mentioned 4-5.

EXAMPLE 6

Antitumour effect against Yoshida's sarcoma.

Cells of Yoshida's sarcoma successively cultured by using Donryu rats were transplanted into the abdominal cavity of all ten rats in each group of Donryu rats at a rate of $1 \times 10^6$ cells/animal, and from after 24 hours of the transplantation each one of the following agents was injected intraperitoneally into each of the rats in groups once every other day in total 10 times. After observing the mortality of the rats, the life-elongating rate of the agent was obtained by calculating the value of dividing the average days of survival of treated rats in one group ($\overline{T}$) by the average days of survival of control ($\overline{C}$) and multiplied by 100, that is, $100 \times \overline{T}/\overline{C}$. The results of the above-mentioned tests are shown in Tables 12 to 16, the agents being chlorambucil and chlorambucil+antibody (Table 12), melphalan and melphalan+antibody (Table 13), a derivative of uramustine and the derivative of uramustine+antibody (Table 14), a derivative of melphalan and the derivative of melphalan+antigen (Table 15) and antibodies themselves (Table 16).

TABLE 12

| Agent | | Amount of administration (mg/kg) | | Life-elongating rate (%) |
|---|---|---|---|---|
| | | Agent | Chlorambucil | |
| Chlorambucil | | 1.0 | 1.0 | 259 |
| Present Compo- | Antibody Rabbit | 10.0 | 0.1 | 230 |
| | *Antibody₃ Rabbit | 10.0 | 0.1 | 238 |

TABLE 12-continued

| | Agent | Amount of administration (mg/kg) Agent | Amount of administration (mg/kg) Chlorambucil | Life-elongating rate (%) |
|---|---|---|---|---|
| sition | *Antibody₁ Rabbit | 10.0 | 0.1 | 240 |
| | Antibody Rat | 10.0 | 0.1 | 235 |
| | *Antibody₁ Rat | 10.0 | 0.1 | 245 |

Note:
*shows that the antibody₁ was purified by the technique of affinity-chromatography (1)

TABLE 13

| | Agent | Amount of administration (mg/kg) Agent | Amount of administration (mg/kg) Melphalan | Life-elongating rate (%) |
|---|---|---|---|---|
| | Melphalan | 1.5 | 1.5 | 230 |
| Present | Antibody Rabbit | 15.0 | 0.15 | 230 |
| Compo- | *Antibody₃ Rabbit | 15.0 | 0.15 | 237 |
| sition | *Antibody₁ Rabbit | 15.0 | 0.15 | 240 |
| | Antibody Rat | 15.0 | 0.15 | 230 |
| | *Antibody₁ Rat | 15.0 | 0.15 | 245 |

TABLE 14

| | Agent | Amount of administration (mg/kg) Agent | Amount of administration (mg/kg) Uramustine | Life-elongating rate (%) |
|---|---|---|---|---|
| | Derivative of uramustine | 5 | 5 | 290 |
| Present | Antibody Rabbit | 50 | 0.5 | 260 |
| Compo- | *Antibody₃ Rabbit | 50 | 0.5 | 264 |
| sition | *Antibody₁ Rabbit | 50 | 0.5 | 265 |
| | Antibody Rat | 50 | 0.5 | 270 |
| | *Antibody₁ Rat | 50 | 0.5 | 285 |

TABLE 15

| | Agent | Amount of administration (mg/kg) Agent | Amount of administration (mg/kg) Melphalan | Life-elongating rate (%) |
|---|---|---|---|---|
| | Derivative of melphalan | 1.5 | 1.5 | 230 |
| Present | Antibody Rabbit | 15.0 | 0.24 | 260 |
| Compo- | *Antibody₃ Rabbit | 15.0 | 0.24 | 278 |
| sition | *Antibody₁ Rabbit | 15.0 | 0.24 | 280 |
| | Antibody Rat | 15.0 | 0.24 | 270 |
| | *Antibody₁ Rat | 15.0 | 0.24 | 290 |

Note:
*shows that Antibody₁ or Antibody₃ in Tables 13–15 was purified by affinity chromatography (1) or (3)

TABLE 16

| Antibody | Amount of administration (mg/kg) | Life-elongating rate (%) |
|---|---|---|
| Rabbit | 5 | 100 |
| * | 5 | 105 |
| Rabbit | 20 | 105 |
| * | 20 | 105 |
| Rat | 5 | 110 |
| * | 5 | 120 |
| Rat | 20 | 120 |
| * | 20 | 120 |

*shows that antibody was purified by affinity chromatography (1) or (3)

As are seen in Tables 12 to 15, the life-elongating rate of the pharmaceutical composition on rats is nearly the same as that of the commercial antitumour substance when administered at a dose rate of 5 to 10 times of that of the commercial antitumour substance, the fact being natural and showing that the tumour-inhibiting activity of the antibody was not exhibited at the degree of the dose rate (see Table 16). The characteristics of the pharmaceutical composition appear clearly when the amount of administration of the commercial antitumour substance as a component of the pharmaceutical composition is compared with the amount of administration of such an antitumour substance itself as the agent. That is, the former is only one tenth or one twentieth of the latter, however, the former gave the substantially same life-elongating rate as the latter. This is the result of the effective translocation of the commercial antitumour substance to the tumour site by the antibody which is another effective component of the pharmaceutical composition, the fact being the realization of the idea of the present invention.

The pharmaceutical composition, owing the above-mentioned function, exhibits the same degree of tumour-inhibiting activity in spite of reducing the use of the ordinary commerciallized antitumour substance to one tenth to one twentieth, the side effects of the ordinary commerciallized antitumour substance being extremely high.

In addition, it should be particularly noted that the occurrence of anaphylactic shock which is experienced in the case where the antibody prepared using rabbits and purified by the usual method was bonded to a commercial antitumour substance and the bonded substance was administered to rats was very much reduced in the case where the antibody was purified by the procedure of affinity chromatography of the present invention. Such a reduction of the occurrence of anaphylactic shocks has been noticed in the case of the antibody against sarcoma-180 in Example 3, and the advantageous effect of affinity chromatography was exhibited again in the case of against Yoshida's sarcoma. In the case where the antibody prepared using mouse and purified by affinity chromatography, the administration of the pharmaceutical composition produced using the antibody did not exhibit any anaphylactic shocks on rats.

EXAMPLE 7

7-1: Preparation and purification of an antibody against tumour cells.

Fifty milliliters of the blood were collected from a male patient suffering from the rectal cancer of age of 50, and 22 ml of an antiserum containing an antibody were obtained from the blood.

7-2: Purification of the antibody by affinity-chromatography (1).

To the freeze-dried tumour extirpated from the above-mentioned patient on operation, 50 ml of 3 M potassium chloride solution buffered by a 5 mM potassium phosphate buffer solution to pH of 7.4 were added to extract the antigen for 20 hours. After centrifugation of the extract liquid for 10 minutes at 65,000 G, the supernatant liquid was collected and dialyzed against distilled water for 72 hours at a temperature of 4° C. (during the dialysis, the external liquid was exchanged every 24 hours). The affinity chromatography of the thus obtained antigen of the patient's tumour was carried out in quite the same manner as in 1-3 of Example 1, except only for using the solution of the antiserum containing the antibody obtained in 7-1 from the patient instead of using the antibody obtained from a mouse.

The thus obtained antibody was also soluble in water but insoluble in organic solvents such as methanol, ethanol, acetone and benzene and showed the infrared and ultraviolet absorption spectra respectively indicated in FIG. 2 and FIG. 3, having a molecular weight of about 150,000 and presenting at Rf of 0 to 0.1 in disc electropholetic diagram.

EXAMPLE 8

8-1: Preparation and purification of an antibody utilizing affinity chromatography (3).

Mitomycin C (50 microgram/ml) was added to the cells of ascites-type P-388 tumour successively cultured by using DBA/2 mice suspended in an aqueous physiological saline solution and after incubating the mixture for 30 minutes at 37° C., the supernatant was removed by centrifugation and the cells were washed 3 times with an aqueous 0.85% physiological saline solution.

The procedures of inoculation of the thus treated cells of P-388 tumour deprived of proliferative activity, to rabbits and the procedures thereafter to obtain the aqueous solution of rabbit's anti-P 388 tumour antibody were quite the same as those in 1-1 of Example 1.

8-2: Cytotoxicity test against tumour cells and normal cells.

Cytotoxicity due to the thus obtained rabbit's antibody against P-388 tumour on cells was examined under the presence of a complement (serum of a guinea pig) by the method already described in 1-2 of Example 1, the results being shown in Table 17.

TABLE 17

| Times of dilution of aqueous solution of antigen | | 1 | 10 | 100 | 1000 |
|---|---|---|---|---|---|
| Antibody solution before purification by affinity chromatography (3) | Cells of P-388 tumour | +++ | +++ | + | — |
| | Cells of spleen of rat | ++ | + | — | — |
| Antibody solution after purification by affinity chromatography (3) | Cells of P-388 tumour | +++ | +++ | ++ | — |
| | Cells of spleen of rat | + | — | — | — |
| Control (Eagle's MEM) | Cells of P-388 tumour | — | — | — | — |
| | Cells of spleen of rat | — | — | — | — |

In addition, the splenic cells of DBA/2 mouse used as the representative of normal cells were treated by the same procedure as those described in 1-2, Example 1.

8-3: Purification of the antibody by using affinity chromatography (1).

The antibody of mouse's anti-P 388 tumour was purified using a column with a carrier to which an antigen of P-388 tumour has been bonded. The procedures themselves were quite the same as those in 1-3 of Example 1, except for using the cells of P-388 tumour successively cultured by using DBA/2 mouse instead of the ascites-type sarcoma-180 cells successively cultured by using ICR mouse.

8-4: Cytotoxicity test against tumour cells and normal cells.

Cytotoxicity due to the rabbit's immuno antibody to P-388 tumour was examined by the same method as in 8-2, the results being shown in Table 18.

TABLE 18

| Times of dilution of solution of antibody | Mortality of Cells | | | | |
|---|---|---|---|---|---|
| | | 1 | 10 | 100 | 1000 |
| Solution of antibody after purification with affinity chromatography (3) | Cells of P-388 tumour | +++ | +++ | ++ | — |
| | Splenic cells of mouse | + | — | — | — |
| Solution of antibody after purification by affinity chromatography (1) | Cells of P-388 tumour | +++ | +++ | ++ | + |
| | Splenic cells of mouse | — | — | — | — |
| Control (Eagle's MEM) | Cells of P-388 tumour | — | — | — | — |
| | Splenic cell of mouse | — | — | — | — |

The above-indicated results show that the activity of the antibody against P-388 tumour cells was remarkably raised and the toxicity of the antibody to the splenic cells was reduced by the purification by affinity chromatography, as in other antibody already mentioned above, indicating the excellent effect of purification due to affinity chromatography (1).

8-5: Bonding of the anti-P-388 tumour antibody to antitumour antimetabolites.

The rabbit's anti-P-388 antibodies prepared by the method of 8-1 and 8-3 and purified by their methods were made to react with each of cytarabine, methotrexate and 5-fluorouracil to synthesize the compounds having an amide bonding between the antibody and the antimetabolite. The followings are the examples of bonding:

SYNTHETIC EXAMPLE 6

Into an aqueous solution containing 10.0 mg of the purified rabbit's anti-P-388 tumour antibody in 1 ml, 20.0 mg of cytarabine were added and then 30 mg of 1-ethyl-3-(3-dimethylaminopropyl) carbodiimide was added to the mixture and made to react for the period shown below, then 2 ml of an aqueous acetic acid-sodium acetate buffer solution was added to stop the reaction. The reaction mixture was dialyzed against 5 liters of distilled water for 72 hours at a temperature of 4° C. (during the dialysis, the external liquid was exchanged every 24 hours). After condensing the internal liquid, it was passed through a column of 1.5 cm in diameter and 55 cm in height packed with a derivative of dextrin (Sephadex G-25, made by Farmacia Japan Co., Ltd.) to adsorb the low-molecular weight substances in the reaction mixture completely onto the column and the effluent was freeze-dried at a temperature of −20° C. to obtain the object substance. The bonded amount of cytarabine as the function of reaction period presumed by the separately carried out results of rec assay are shown in Table 19.

TABLE 19

| Period of reaction (min) | Cytarabine (microgram)/antibody (mg) |
|---|---|
| 10 | 4.8 |
| 30 | 8.2 |
| 60 | 11.0 |

SYNTHETIC EXAMPLE 7

Into an aqueous solution containing 10 mg of rabbit's antibody against P-388 tumour prepared and purified in 8-1 of Example 8 in one ml, 6.0 mg of methotrexate was added and while adjusting the pH of the solution to 4.75 by the addition of hydrochloric acid under agitation 2.5 mg of 1-ethyl-3-(3-dimethylaminopropyl) carbodiimide hydrochloride was added to make reaction for the period shown below. The reaction was then stopped by the addition of 2 ml of an aqueous acetic-sodium acetate buffer solution. The reaction mixture was dialyzed against 5 liters of distilled water for 72 hours at a temperature of 4° C. (during the dalysis, the external liquid was exchanged every 24 hours).

The dialyzed internal liquid was treated as in Synthetic Example 6 above to obtain the object pharmaceutical composition. The amount of bonded methotrexate was shown in Table 20 as a function of reaction period.

TABLE 20

| Period of reaction (min) | Methotrexate (microgram)/antibody (mg) |
|---|---|
| 10 | 3.6 |
| 30 | 6.5 |
| 90 | 15.0 |

SYNTHETIC EXAMPLE 8

Bonding 5-fluorouracil to the antibody.

Using the rabbit's antibody against P-388 tumour prepared and purified in 8-1 of Example 8 and 34.7 mg of 5-fluorouracil, a reaction was carried out in the same manner as in Synthetic Example 7, however, the obtained product substantially did not contain 5-fluorouracil moiety. Then, after introducing a carboxyl group into 5-fluorouracil by the following procedure, the bonding reaction was performed in the same manner as in 8-1, Example 8. The thus obtained bonded pharmaceutical composition contained 10 microgram of 5-fluorouracil per mg of the antibody.

The carboxylated 5-fluorouracil was synthesized as follows:

To 10 ml of methanol, 500 mg of 5-fluorouracil and 86 mg of potassium hydroxide were added and 3 ml of distilled water was added to the mixture. To the thus formed transparent liquid, 145 mg of chloroacetic acid were added at once and the mixture was agitated for 60 hours at the room temperature. After the reaction was over, the reaction mixture was condensed under reduced pressure and the residue was recrystallized from ethanol and chloroform to obtain 495 mg (yield of 49%) of white crystals identified as the compound having the following structure by infrared spectroscopy and elementary analysis:

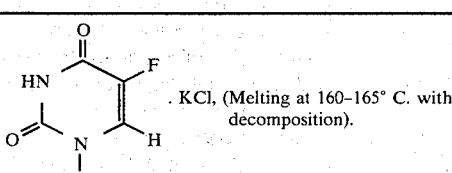

. KCl, (Melting at 160–165° C. with decomposition).

| Elementary analysis | C | H | N |
|---|---|---|---|
| Found: | 27.40% | 2.00% | 10.30% |
| Calcd ad $C_6H_5N_2O_4KCl$ | 27.43 | 1.91 | 10.66 |

SYNTHETIC EXAMPLE 9

The rabbit's antibody against P-388 tumour prepared and purified in 8-3, Example 8 was made to react with each of cytarabine, 8-azaguanine, methotrexate, aminoputerin sodium and the derivative of 5-fluorouracil (refer to Synthetic Example 8) to obtain each bonded pharmaceutical composition, which was almost similar to the pharmaceutical composition obtained by Synthetic Examples 6 to 8.

EXAMPLE 9

9-1: Preparation and purification of an antibody to tumour cells.

Ascites-type P-388 tumour cells successively cultured by using DSA/2 mice and deprived of their proliferative activity by mitomycin C were inoculated intraperitoneally into a DBA/2 mouse once a week at a rate of $10^7$ cells/animal, and after 7 days of the fourth inoculation the blood was collected from the abdominal large vein on its laparotomy under anesthesia, and the antiserum containing the antibody was prepared from the blood. Total amount of antiserum was 53 ml from 100 mice. The preparation and purification of the antibody from the antiserum were carried out in the same manner as in 8-1, Example 8.

9-2: Purification of the antibody by affinity chromatography:

The freeze-dried cells of ascites-type P-388 tumour were treated in the same manner as the cells of Yoshida's sarcoma in 4-3, Example 4, however, omitting the salting-out by ammonium sulfate and the centrifugation thereafter. Thus, an aqueous solution of the antibody against ascites-type P-388 tumour purified by affinity-chromatography was obtained.

9-3: Disturbance test against tumour cells and normal cells.

Disturbance due to the mouse's antibody against ascites-type P-388 tumour obtained in 9-2 above was examined by the same method as in Example 1, the results being shown in Table 21.

TABLE 21

| | | Mortality of Cells | | | |
|---|---|---|---|---|---|
| Times of dilution of solution of antibody | | 1 | 10 | 100 | 1000 |
| Antibody before purification by affinity chromatography (1) | Cells of P-388 tumour | +++ | ++ | — | — |
| | Splenic cells of mouse | — | — | — | — |
| Antibody after purification by affinity chromatography (1) | Cells of P-388 tumour | +++ | +++ | ++ | + |
| | Splenic cells of mouse | — | — | — | — |
| Control (Eagle's MEM) | Cells of P-388 tumour | — | — | — | — |
| | Splenic cells of mouse | — | — | — | — |

As is seen in Table 21, the activity of the antibody against P-388 tumour cells was remarkably raised by the procedures of affinity chromatography as in the preceeding Examples.

9-4: Bonding of mouse's antibody against P-388 tumour to antitumour antimetabolites.

The mouse's antibodies against P-388 tumour obtained by the procedures in 9-1 and 9-2, Example 9 were respectively bonded to each of the antimetabolites, that is, cytarabine, methotrexate, aminoputerin sodium, 8-azaguanine and 5-fluorouracil in the same manner as that described in 8-5, Example 8 to obtain pharmaceutical composition in which the antibody is bonded to the antimetabolite with an amide bond. These pharmaceutical composition showed almost the same physicochemical properties as those of the corresponding pharmaceutical composition obtained in 8-5, Example 5.

EXAMPLE 10

Antitumour effect of the pharmaceutical composition against P-388 tumour.

Cells of the P-388 tumour cells successively cultured by using DBA/2 mice were transplanted into the abdominal cavity of each 10 DBA/2 mice of each group at a rate of $1 \times 10^6$ cells/animal, and from after 24 hours of the transplantation, an aqueous solution of each of the following antitumour agents was intraperitoneally administered to the mouse once a day for 5 consecutive days, in total of five times, and after observing the mortality of the mice the average survival days of treated group of mice ($\overline{T}$) and those of control (transplanted, however, not administered) ($\overline{C}$) were obtained to calculated the life-elongating rate ($100 \times \overline{T}/\overline{C}$). The results are shown in Tables 22 to 26, Table 26 showing the results of administering only the antibody.

The antitumour agents used in this Example are:

(1) Antimetabolic antitumour agents: cytarabine, methotrexate, aminoputerin sodium and derivative of 5-fluorouracil, (2) Bonded pharmaceutical composition of the rabbit's antibody not purified by affinity chromatography to one of the above-mentioned antimetabolic antitumour agents, (3) Bonded pharmaceutical composition of the rabbit's antibody purified by affinity chromatography (1) to one of the above-mentioned antimetabolic antitumour agents, (4) Bonded pharmaceutical composition of the mouse's antibody not purified by affinity chromatography to one of the above-mentioned antimetabolic antitumour agents, and (5) Bonded pharmaceutical composition of the mouse's antibody purified by affinity chromatography (1) to one of the above-mentioned antimetabolic antitumour agents.

TABLE 22

| Agent | | Amount of administration | | Life-elongating Rate (%) |
|---|---|---|---|---|
| | | Agent (mg/kg) | Cytarabine (mg/kg) | |
| Cytarabine | | 20 | 20 | 220 |
| Present Composition | Rabbit's Antibody | 200 | 2 | 200 |
| | *Rabbit's Antibody | 200 | 2 | 210 |
| | Mouse's Antibody | 200 | 2 | 210 |
| | *Mouse's Antibody | 200 | 2 | 215 |

Note:
*indicates that the antibody has been purified by affinity chromatography (1).

TABLE 23

| Agent | | Amount of administration | | Life-elongating Rate (%) |
|---|---|---|---|---|
| | | Agent (mg/kg) | Methotrexate (mg/kg) | |
| Methotrexate | | 3 | 3 | 250 |
| Present Composition | Rabbit's Antibody | 30 | 0.3 | 190 |
| | *Rabbit's Antibody | 30 | 0.3 | 210 |
| | Mouse's Antibody | 30 | 0.3 | 230 |
| | *Mouse's Antibody | 30 | 0.3 | 240 |

TABLE 24

| Agent | | Amount of administration | | Life-elongating Rate (%) |
|---|---|---|---|---|
| | | Agent (mg/kg) | Aminopterin sodium | |
| Aminopterin sodium | | 3 | 3 | 270 |
| Present Composition | Rabbit's Antibody | 30 | 0.3 | 240 |
| | *Rabbit's Antibody | 30 | 0.3 | 245 |
| | Mouse's Antibody | 30 | 0.3 | 250 |
| | *Mouse's Antibody | 30 | 0.3 | 260 |

TABLE 25

| Agent | | Amount of administration | | Life-elongating Rate (%) |
|---|---|---|---|---|
| | | Agent (mg/kg) | Aderivative of 5-fluorouracil(mg/kg) | |
| Aderivative of 5-fluorouracil | | 50 | 50 | 185 |
| Present Composition | Rabbit's Antibody | 500 | 5 | 160 |
| | *Rabbit's Antibody | 500 | 5 | 170 |
| | Mouse's Antibody | 500 | 5 | 165 |
| | *Mouse's Antibody | 500 | 5 | 180 |

TABLE 26

| Antibody | Dose rate (mg/kg) | Life-elongating rate (%) |
|---|---|---|
| Rabbit | 5 | 100 |
| * | 5 | 105 |
| Rabbit | 20 | 105 |
| * | 20 | 105 |
| Mouse | 5 | 110 |
| * | 5 | 120 |
| Mouse | 20 | 120 |
| * | 20 | 120 |

Note:
*Shows that the antigen was purified by affinity chromatography (1)

The characteristic feature of the pharmaceutical composition does at first appear when the amount of administration of the commercial antitumour agent itself is compared to the amount of administration of the same antitumour agent as a component of the pharmaceutical composition. In spite of the fact that the latter is only one tenth to one twentieth of the former, the life-elongating rate due to the latter is almost equal to that due to the former. The fact is the reflection of the phenomenon that the antibody favorably transfers the commercial antitumour agent to the tumour site in the animal body, and the excellent realization of the idea of the present invention. The pharmaceutical composition, owing to the above-mentioned function, exhibits its antitumour activity to the same degree as the commercial antitumour agent having an extremely high side effects while reducing the use of such a commercial antitumour agent to one tenth-one twentieth.

In addition, it should be especially noticed that in the case where the antibody prepared by using rabbit is bonded to each of the commercial antitumour agents and administered to mice, anaphylactic shock such as general spasm and stiffening appears on about 3 mice among 10 mice, however, the pharmaceutical composition produced by bonding the same antitumour agent with the antibody prepared by using rabbit and purified by affinity chromatography does not appear substantially such anaphylactic shocks. The pharmaceutical composition produced by bonding the antibody prepared by using mouse and purified by affinity chromatography with the same commercial antitumour agent never gave such anaphylactic shocks. These findings have been experienced already in Examples 3 and 6, and the reason is the reflection of the effectiveness of the affinity chromatography in removing the cause of such anaphylactic shock.

What is claimed is:

1. A pharmaceutical composition having antitumor activity without causing pyrexia and anaphylaxis which comprises antitumor antibodies purified by affinity-chromatography bound to an antitumor substance having at least one amino group or carboxyl group by amide bonding.

2. A pharmaceutical composition according to claim 1 wherein said antitumor antibody is obtained by purifying immunoglobulin G fraction with affinity-chromatography.

3. A pharmaceutical composition according to claim 1 or 2, wherein said antitumor antibody is an antitumor alloantibody purified by affinity-chromatography.

4. A pharmaceutical composition according to claim 1, wherein said antitumor substance is a member selected from the group consisting of antibiotic substances, antimetabolitic substances and alkylating agents.

5. A pharmaceutical composition according to claim 1, wherein the amino group or the carboxyl group of said antitumor substance is introduced thereinto by bringing the antitumor substance into reaction with a compound having the formula:

$$X(CH_2)_n COOH$$

wherein X represents an atom of chlorine or bromine and n denotes an integer of 1 to 3.

6. A pharmaceutical composition according to claim 1, wherein the amino group or the carboxyl group of said antitumor substance is introduced thereinto by bringing the antitumor substance into reaction with a compound having the formula:

$$HCl \cdot NH_2(CH_2)_n COX$$

wherein X represents an atom of chlorine or bromine and n denotes an integer of 1 to 3.

7. A pharmaceutical composition according to claim 1, wherein said affinity-chromatography is performed by using a carrier to which molecules of the tumor antigen are bound.

8. A pharmaceutical composition according to claim 7, wherein said carrier is packed into a column.

* * * * *